US012672983B2

(12) United States Patent
Albertsson et al.

(10) Patent No.: US 12,672,983 B2
(45) Date of Patent: Jul. 7, 2026

(54) SLEEVE OR LINER FOR AN ARTICLE

(71) Applicant: OSSUR ICELAND EHF, Reykjavik (IS)

(72) Inventors: Halldor Albertsson, Reykjavik (IS); Valgeir Petursson, Reykjavik (IS); Sindri Pall Sigurdsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 7 days.

(21) Appl. No.: 18/669,130

(22) Filed: May 20, 2024

(65) Prior Publication Data

US 2024/0307234 A1      Sep. 19, 2024

Related U.S. Application Data

(63) Continuation of application No. PCT/US2022/051386, filed on Nov. 30, 2022.

(60) Provisional application No. 63/284,714, filed on Dec. 1, 2021.

(51) Int. Cl.
     *A61F 13/04*          (2006.01)
     *A61F 13/06*          (2006.01)
(52) U.S. Cl.
     CPC .......... *A61F 13/041* (2013.01); *A61F 13/061* (2013.01)
(58) Field of Classification Search
     CPC .... A61F 5/0123; A61F 5/0102; A61F 5/0104; A61F 5/0106; A61F 5/0109; A61F 5/30; A61F 5/32; A61F 2002/785
     See application file for complete search history.

(56) References Cited

U.S. PATENT DOCUMENTS

| | | | |
|---|---|---|---|
| 4,887,590 A | 12/1989 | Logue et al. | |
| 8,425,441 B2 | 4/2013 | Ingimundarson | |
| 2002/0082542 A1* | 6/2002 | Hall ........................ | B32B 37/24 |
| | | | 602/75 |
| 2006/0070164 A1* | 4/2006 | Nordt, III ............. | A61F 5/0106 |
| | | | 2/69 |
| 2007/0225824 A1* | 9/2007 | Einarsson ................ | A61F 2/78 |
| | | | 623/36 |
| 2009/0054819 A1* | 2/2009 | Einarsson ............. | A61F 5/0123 |
| | | | 602/5 |
| 2010/0217169 A1 | 8/2010 | Ingimundarson | |
| 2013/0165018 A1* | 6/2013 | Barker ...................... | A61F 5/03 |
| | | | 450/95 |
| 2014/0005583 A1* | 1/2014 | Cardinali ............. | A61F 5/0123 |
| | | | 602/5 |
| 2016/0206448 A1 | 7/2016 | Klutts | |
| 2017/0348130 A1 | 12/2017 | Petursson | |
| 2018/0042754 A1 | 2/2018 | Ingimundarson et al. | |

(Continued)

OTHER PUBLICATIONS

International Search Report from corresponding PCT Application No. PCT/US2022/051386, Feb. 24, 2023.

*Primary Examiner* — Kari K Rodriquez
(74) *Attorney, Agent, or Firm* — Workman Nydegger

(57)                    ABSTRACT

A sleeve or liner for a brace component in an orthopedic device, such that the brace component defines a peripheral contour and forms at least one unique feature. The sleeve or liner includes a main body having a peripheral contour arranged at least approximately to the peripheral contour and in size of the brace component. A predetermined pattern of frictional elements is formed by deposits, or a film of frictional material configured in at least one predetermined shape.

15 Claims, 6 Drawing Sheets

(56) References Cited

U.S. PATENT DOCUMENTS

2019/0105188 A1    4/2019   Petursson et al.
2019/0358062 A1    11/2019  Klutts

* cited by examiner

284

280

282

286

290

294

296

292

300

306

302

304

SLEEVE OR LINER FOR AN ARTICLE

FIELD OF THE DISCLOSURE

The disclosure relates to a sleeve for an orthopedic device or another relevant article, particularly a sleeve with a predetermined pattern of frictional elements.

BACKGROUND

Known orthopedic devices provide stability, protection, support, rehabilitation, and unloading of a portion of the human anatomy. However, these known devices are often considered uncomfortable, physically bulky, heavy, not durable, tedious, and difficult to adjust, and costly, requiring numerous manufacturing processes to be produced.

An example of an orthopedic device is a knee brace. Knee braces are widely used to treat many knee infirmities. Such braces may be configured to impart forces or leverage on the limbs surrounding the knee joint to relieve compressive forces within a portion of the knee joint or reduce the load on that portion of the knee. If knee ligaments are weak and infirm, a knee brace may stabilize, protect, support, unload, and rehabilitate the knee.

Examples of such orthopedic devices are found in US patent application publication 2019/0358062, published on Nov. 28, 2019; US patent application publication 2017/0348130, published on Dec. 7, 2017; and US patent application publication 2019/0105188, published on Apr. 11, 2019, U.S. Pat. No. 8,425,441, granted on Apr. 23, 2013, each of the preceding patent application publications and patent is incorporated herein by reference.

Strapping systems are commonly used to secure orthopedic devices to the user's anatomy. Unfortunately, few changes have been made to strapping systems, and more focus needs to be given to improving strapping. Rather, the emphasis on orthopedic devices often relates to the frame structure and methods for preventing migration of the orthopedic device on the user during use, and strapping systems are typically off-the-shelf products, with little to no focus devoted thereto.

Typically, orthopedic devices include a cushioned interface for the user to relieve the pressure exerted by the straps and frame, particularly as straps are tensioned, and the user undergoes activity. The cushion interfaces are often comprised of foam. They may include frictional features such as the inherent texture or properties of the cushion interface, or frictional materials are added to the cushion interfaces to prevent migration.

The cushion interfaces typically have a consistent thickness across their intersection with the frame of the orthopedic device and do not accommodate areas of the orthopedic device prone to building pressure on the user. In addition, such cushion interfaces may likewise be heavy, make the orthopedic device more cumbersome for consistent wearing, and lead to clumsy proprioception.

As discussed in US patent application publication 2019/0358062, liners including vapor permeability and frictional characteristics exist for orthopedic and prosthetic devices and serve as a padded interface between an orthopedic or prosthetic device and the skin of a user. While these liners exist, many must compromise vapor permeability and frictional characteristics due to the limitations of materials involved. These solutions balance the costs of materials used, their characteristics, and the processes employed for making the liners. Unfortunately, only some solutions have been able to produce a low-cost liner, simple to manufacture and possesses suitable characteristics, including breathability, compressibility or padding, and desirable frictional properties.

U.S. Pat. No. 8,425,441 refers to a sleeve, liner, or cushion interface as a spacer element. According to one embodiment, the knee brace is provided with at least one breathable spacer element having an inner surface connected to an inner-facing surface of at least one of the proximal and distal members. The spacer element defines an outer surface opposing the inner surface and includes a frictional feature or layer coated over a mesh layer of the breathable material forming the spacer element. The mesh layer includes defined apertures, and the coating thereof by the frictional material corresponds to the apertures, thereby forming an apertured surface with a frictional material that must not occlude the apertures of the mesh layer. Because the frictional material coats the mesh layer, it tends to be thick, which can lead to aggressive frictional properties against the skin of the user.

There is a need for a sleeve, liner, or cushion interface, collectively referred to as a sleeve in this disclosure, adapted for orthopedic or prosthetic devices or another type of wearable article having desired areas for additional reinforcement against a user to accommodate pressure distribution, providing enhanced proprioception, and maintaining the device in the desired configuration on the user.

SUMMARY

The sleeve, liner, or cushion interface embodiments described may be used in various prosthetic or orthopedic applications. The liner embodiments may also be provided with no relationship to a particular prosthetic or orthopedic device and used in various articles where frictional control, breathability, compression, or padding is required or desired.

BRIEF DESCRIPTION OF THE DRAWINGS

These and other features, aspects, and advantages of the embodiments of the disclosure will become readily apparent and better understood given the following description, appended claims, and accompanying drawings.

DETAILED DESCRIPTION OF VARIOUS EMBODIMENTS

Figure 1:
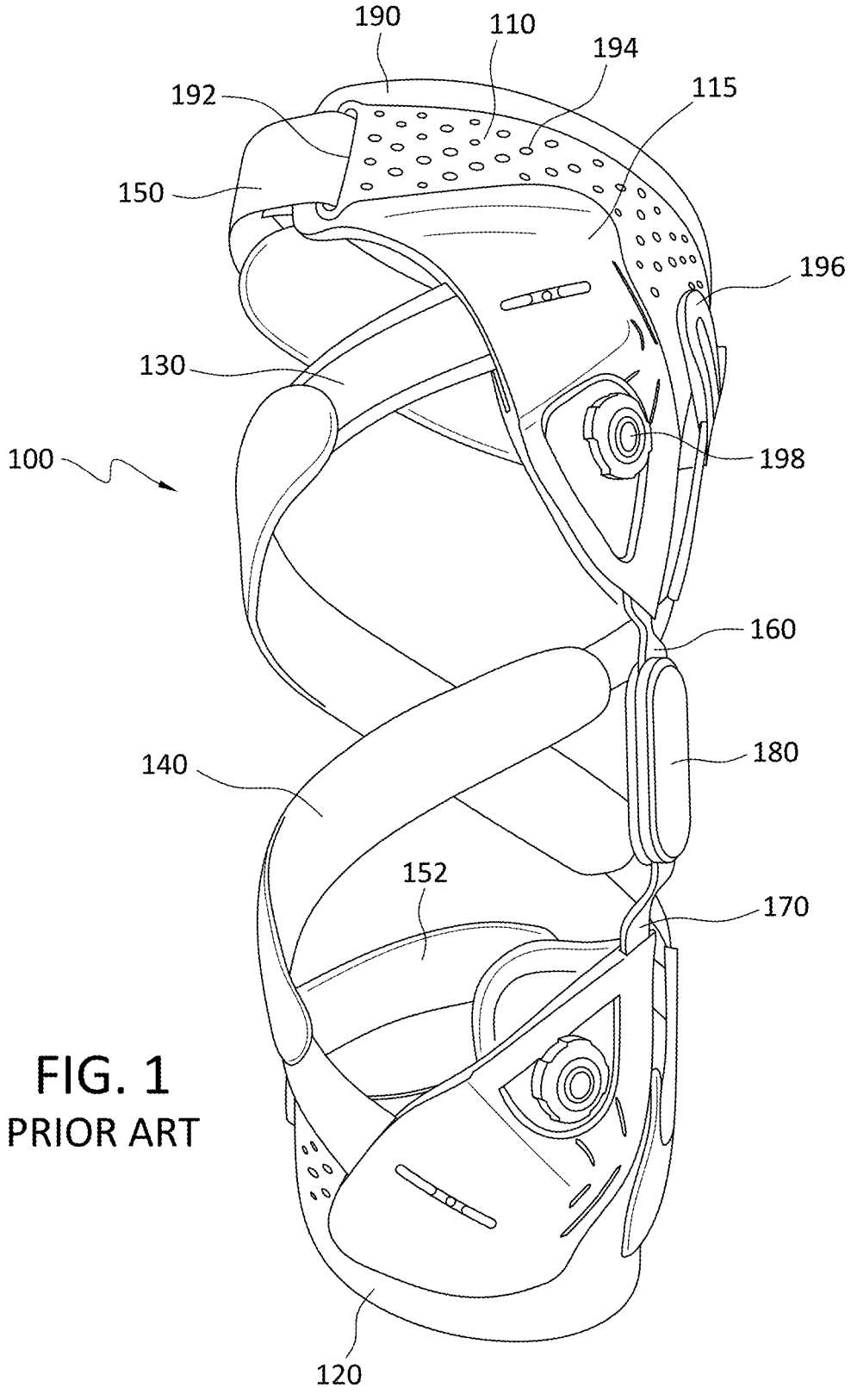
FIG. 1 is a perspective view of a prior art orthopedic device, including brace components and unique features attached thereto for use with a sleeve of the disclosure.

A better understanding of different embodiments of the disclosure may be had from the following description read with the accompanying drawings in which like reference characters refer to like elements.

While the disclosure is susceptible to various modifications and alternative constructions, certain illustrative embodiments are shown in the drawings and will be described below. It should be understood, however, there is no intention to limit the disclosure to the embodiments disclosed, but on the contrary, the intention is to cover all modifications, alternative constructions, combinations, and equivalents falling within the spirit and scope of the disclosure and defined by the appended claims.

It will be understood that unless a term is defined in this patent to possess a described meaning, there is no intent to limit the meaning of such term, either expressly or indirectly, beyond its plain or ordinary meaning.

Exemplary Orthopedic Device

An example of an orthopedic device 100 is drawn from US patent application publication 2019/0105188. According to the depicted embodiment, the orthopedic device 100 includes a first shell or brace component 110, such as a thigh shell, a second shell or brace component 120, such as a calf shell, and a hinge 180 connecting to the first and second shells 110, 120 by first and second struts 160, 170.

A first strap or dynamic force strap 130 has a first end slidably connecting to the first shell 110 and a second end removably anchoring to the second shell 120. An overlay 115 extends over a portion of the first and second shells 110, 120 and forms a clearance with the first and second shells 110, 120 into which the first ends of the first dynamic force strap 130 and a second dynamic force strap 140 extend.

To reduce the bulkiness of the orthopedic device 100 and provide a more stable platform for tensioning the dynamic force straps 130, 140, a cable connects the dynamic force straps 130, 140 to a tensioning mechanism 198. The tensioning mechanism 198 is attached to the shells 110, 120 and confines the cable and the travel thereof within the shells 110, 120.

The orthopedic device 100 has a first circumferential strap 150 connecting to opposed sides of the first shell 110 to create a circumference with the first shell 110. The circumferential strap 110 has a first end securing to the first shell 110 by a slot 192, and a second end releasably connecting to the first shell 110 by a first connector or buckle 196. An end of the first strap 130 also connects to the first connector 196. A second connector, analogous to the structure of the first connector 196, releasably connects a second end of a second circumferential strap 152 and the first dynamic force strap to the second shell 120. Like the first circumferential strap 150, the first end of the second circumferential strap 152 may secure to the second shell 120.

The first shell 110 may define a peripheral edge 190 extending about the first shell body, so the peripheral edge 190 is more flexible than the first shell body. The first shell body 128 is preferably rigid or semi-rigid. A liner (not shown) may be located on an inner surface of the orthopedic device 100 and the first shell 110. The first and second shells

110, 120 may also define a ventilation feature 194, including a series of apertures extending through a thickness, such as the entirety, of the shells.

Figure 2:
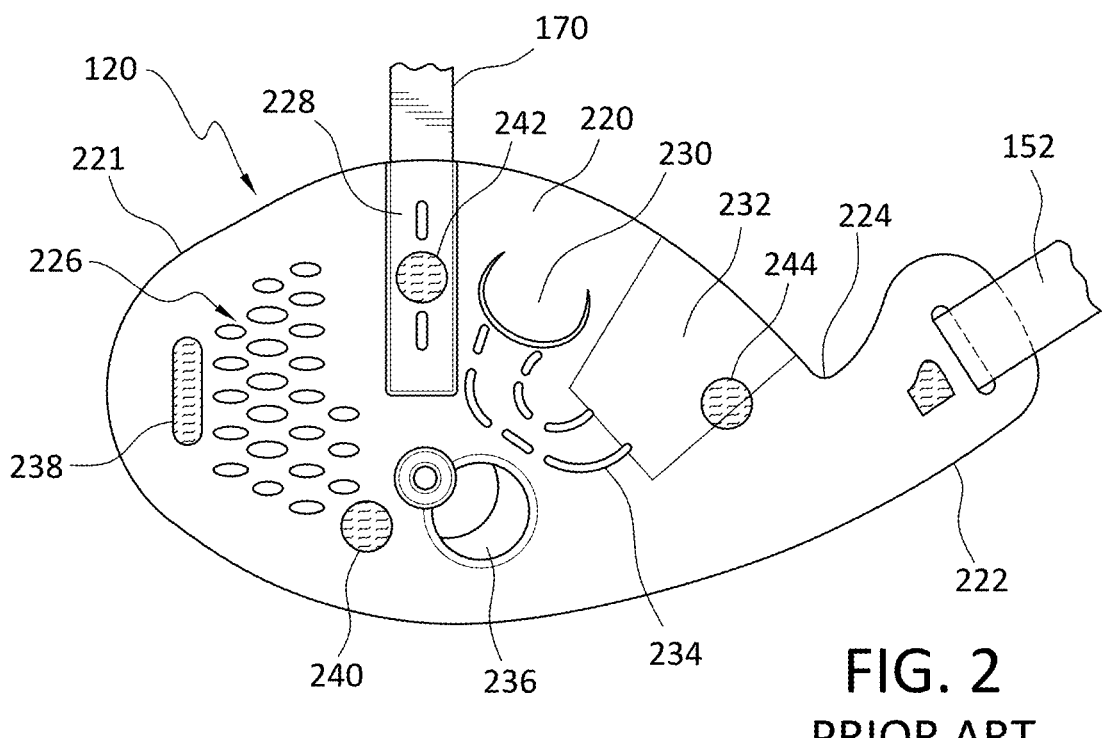
FIG. 2 is a detailed schematic view of a prior art brace component in the orthopedic device of FIG. 1.

FIG. 2 exemplifies the unique features associated with the first and second shells in FIG. 1. The exemplary shell 120 has a main body 220 with a peripheral contour 221, including an extension 222 and a junction 224 to the main body 220. The main body includes a ventilation feature 226, as described above. A strut contour 228 is provided for accommodating the strut 170 and may result in a sleeve or bulge according to the strut 170. A tensioning mechanism mount area 230 includes an area 232 for the overlay in FIG. 1, and channels 234 for routing the cable. A buckle mount 236 is provided for receiving the buckle 196. Hook areas 238, 240, 242, 244, are either formed by the main body itself with an integrated hook relief, recesses in the main body for receiving hook patches secured thereto, or areas for placement of hook patches.

Sleeve Embodiments

According to embodiments described herein, a sleeve may be provided to secure about a shell, as described in connection with FIGS. 1 and 2. The sleeve can provide additional reinforcement in desired areas against the limb of a user with more even pressure distribution for enhanced proprioception and to maintain the device in the desired configuration. For instance, a sleeve may be removable from the shells or other forms of brace components to offer the desired pressure distribution.

The sleeve may be constructed from a variety of materials. In a preferred embodiment, the liner is a lamination that includes a micro jersey (polyester), open cell foam (PU), and unbroken loop material (UBL), which may be formed by nylon. However, all such layers may not be consistently laminated together. For example, there may be areas of just the micro jersey, or micro jersey and PU foam, or micro jersey and UBL, or any combination thereof. Silicone may coat at least one portion of the micro jersey, and such silicone may be silk printed, or 3D printed, or any other type of deposition, onto the micro jersey. The sleeve is preferably selected to permit crisp and defined portions of silicone to be deposited thereon.

The sleeve is preferably breathable and elastic. The stiffness may be around OOO 50. The sleeve may be soft and provide cushioning. A portion of the sleeve may include the UBL, which is arranged to engage with hook elements provided on the orthopedic device. Alternatives to a hook-and-loop connection include a hook and opening arrangement, frictional fit by the elasticity of the sleeve, providing an overmolded brim along the outer side of the liner, which is a portion of the orthopedic device can slide into and engage, or any other suitable manner.

The sleeve may be adapted to secure about a shell, including inner (side adjacent the user) and outer surfaces, or may be arranged to secure only to the inner surface of the shell. For example, if securing about the shell's inner and outer surfaces, the sleeve may envelop both surfaces by sliding over and securing thereabout, such as by elastic edges or other suitable means for securing the sleeve over the shell, such as fasteners including hook and loop or other types. A textile belonging to the sleeve may extend over the outer surface and cover at least part of the shell, and the inner side of the sleeve may include appropriate padding and/or frictional characteristics to inhibit sliding or migration against the leg of a wearer.

For securing along a surface, such as only the inner surface of the shell, the sleeve may form a liner or liner pad, adapted to the shape of the periphery of the shell, being sized slightly larger (i.e., the periphery of the liner being 1 to 10 mm beyond the periphery of the shell), the same size, or slightly smaller (i.e., periphery of the liner being 1 to 10 mm less than the periphery of the shell). Fastener means, such as hook and loop, may be applied to corresponding liner surfaces and the shell.

In an alternative, the liner pad may have peripheral edges that have elasticity, and the peripheral edges can resiliently and elastically secure over a limited portion of the outer surface of the shell, and retain the liner therewith, while generally extending over or entirely over the inner surface of the shell.

For case of simplicity in the following discussion, the sleeve and liner are used interchangeably as the corresponding component to the sleeve and liner may envelop at least part of the outer surface of the shell and extend along an inner surface of the shell or may only be generally delimited along the inner surface of the shell, apart from the aforementioned alternative whereby the peripheral edges.

Figure 3:
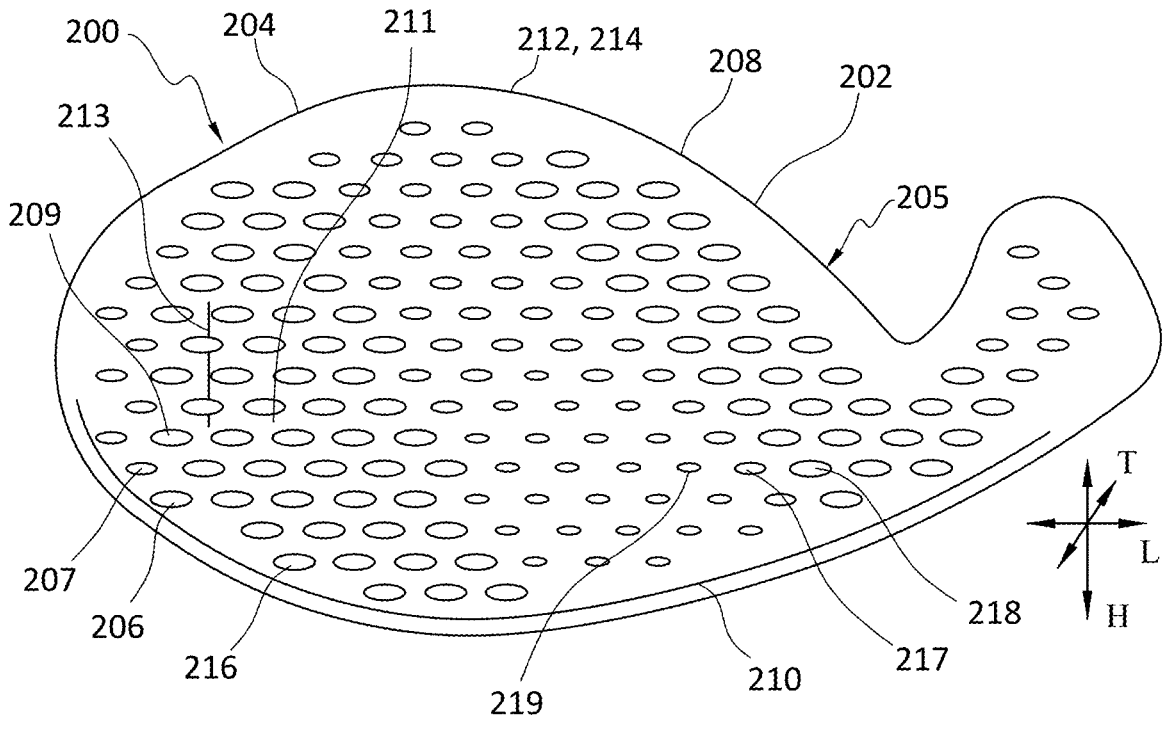
FIG. 3 is a plan view of a first side of a sleeve embodiment, including a predetermined pattern of frictional elements corresponding to a brace component of FIG. 1.

FIG. 3 illustrates an embodiment of a sleeve 200 for a brace component, such as the shells in FIGS. 1 and 2 in an orthopedic device 100. As noted, the brace component 110, 120 defines a peripheral contour 221 and forms or has at least one unique feature, such as various shapes of the main body, junction, or extension, as well as corresponding to the ventilated feature, slots, or bulges, mounting areas, housings, channels, or attachment areas.

The sleeve 200 has a main body 202 defining a peripheral contour 208 arranged at least approximate to the peripheral contour 221 and in size of the brace component 110, 120. A predetermined pattern 206 of individual frictional elements or deposits of frictional material 216 are disposed about the main body 202. The predetermined pattern 206 may be dictated according to the shape of the brace component, properties of the brace component such as flexibility, pressure mapping of the brace component, or any one of the unique features.

The main body 202 forms first and second faces 212, 214, whereby at least one of the faces includes the predetermined pattern 216. Such face, including the predetermined pattern, is intended to be placed adjacent to the user and would extend along the interior side of a brace component yet face outwardly toward the user. The other face opposite the face having the predetermined pattern covers an exterior side of the brace component and may be suitably configured without a predetermined pattern or in a manner capable of withstanding wear on the exterior of the orthopedic device. The faces are preferably mirror images of each other and may be secured along their peripheral edges.

Alternatively, only the face bearing the predetermined pattern may be sized to cover the brace component. The other face may only partially extend about the brace component's exterior side. For example, the periphery of the other face may be elastic and fits over the periphery of the brace component, and elastically secure therewith. The periphery may include frictional material to enhance its engagement with the brace component. Of course, other configurations of the other face can ensure that the face with the predetermined pattern does not move relative to the brace component.

The main body may be formed from a textile material or otherwise breathable material to permit air and moisture transfer between and out from the first and second faces. The main body may include the construction of different material about the edge that is more durable than other material forming the main body to permit easy air transfer. The frictional elements may be formed from a material that creates greater friction than the material or materials forming the body. The frictional material should be skin-friendly so as not to create discomfort to the user yet has sufficient property to frictionally engage the skin of a user even during sweat to maintain the orthopedic device on the user.

The main body 202 of the sleeve 200 preferably corresponds in shape to at least a portion of the main body 220 of the brace component 110, 120. Alternatively, the sleeve may correspond entirely to the shape of the brace component. Preferably, to discourage migration of the sleeve relative to the brace component, the sleeve snugly fits the brace component and is sized and configured accordingly. Moreover, there may be frictional material or other means on the inside surface of the sleeve to discourage movement relative to the brace component, aside from close-fitting of the sleeve on the brace component.

Figures 7A, 7B, 7C, 7D, 8, 9:
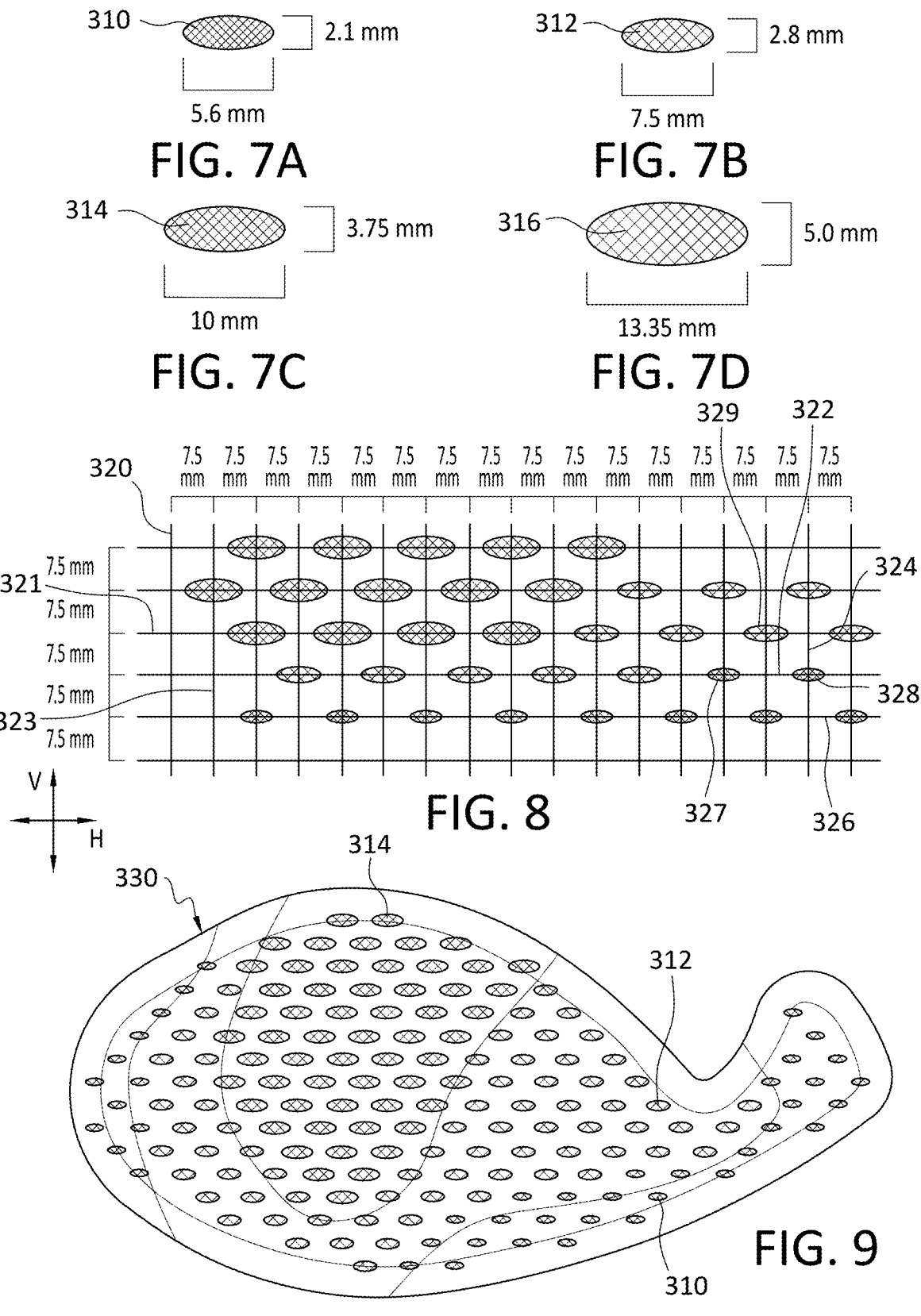
FIGS. 7A-7D illustrate different exemplary-sized frictional elements.
FIG. 8 is a schematic view illustrating a grid along which the frictional elements are arranged in predetermined patterns.
FIG. 9 is a schematic view showing the frictional elements in FIGS. 7A-7D arranged along the grid of FIG. 8.

The frictional elements 216 are configured in at least one predetermined shape. The predetermined shape may be the same for all frictional elements of the predetermined pattern, and they may differ only according to size. Alternatively, the frictional elements 216 may vary according to shape or size. For example, as shown in FIG. 8, the frictional elements may be arranged in horizontal rows and vertical columns in a grid-like manner according to the predetermined characteristics of the shell and the manner in which it is worn. Such frictional elements 216 may vary along either the rows or columns.

The frictional elements 216 are arranged to protrude from the main body 202 and the corresponding face on which the predetermined pattern 206 is placed. Thus, the frictional elements 216 have a thickness T protruding away from the face toward the user. The thickness T of an individual frictional element 216 may vary according to their overall surface area and/or size. Alternatively, all frictional elements 216 of a certain size and surface area may have the same thickness T.

As shown in FIG. 3 and at least FIGS. 7A-7D, the frictional elements 216, 310, 312, 314, 316 may preferably have an oval shape that is generally or just the same shape. The oval shape is preferably elongated in the horizontal H or length L directions of the sleeve. The shape is not limited to an oval, and other shapes are possible, and can be arranged differently relative to the horizontal H or length L, or vertical V or height H of the sleeve. Indeed, the predetermined pattern 206 may have frictional elements of not only different sizes, as evidenced by the possibilities in FIGS. 7A-7D, but the frictional elements may have different shapes within the predetermined pattern. However, according to the preferred embodiment of FIG. 3, the frictional elements 216 all share the same shape, albeit in different sizes.

FIGS. 3, 8 and 9 illustrate the predetermined pattern 206 arranged in rows of frictional elements 206. For example, first and second rows 207, 209 have frictional elements 216. Therefore, the first row 207 is staggered in a vertical V or height H direction of the sleeve 200 relative to the frictional elements 216 of the second row 209 with a spacing 211 between each of the frictional elements in the first row 207 lining up in the height H direction to the sleeve to the frictional elements of frictional material 216 in the second row 209.

For example, the first and second frictional elements 217, 218 are arranged in the first row, and are adjacent to one another along the length L direction. A third frictional element 219 is arranged in the first row and has a different size than the first and second frictional elements 217, 218.

FIG. 8 in view of FIG. 3 shows how the frictional elements are preferably aligned to a cartesian grid 320, in that each row 321 is uniformly spaced and has a plurality of frictional elements at predetermined locations regardless of their size and shape. Each row is intersected by columns 323 which are uniformly spaced from one another. It follows that first and second frictional elements 327, 328 are spaced apart with a spacing 322 from one another along a row based on the columns, as is a third frictional element 329 in a row above the first and second frictional elements 327, 328. The third frictional element 329 is equidistant to the first and second frictional elements 327, 328, and spaced vertically by a spacing 324. The spacings 322, 324 may vary depending on the size of the frictional elements 216, as evidenced by FIG. 8.

The preferable grid configuration allows for consistency when configuring the predetermined pattern and allows the pattern to be tailored to accommodate different flexibility gradients and pressure mapping of the brace component.

The sleeve 200 may include an edging 204 surrounding the predetermined pattern 206 and be devoid of frictional material to facilitate donning of the orthopedic device with the sleeve. The frictional elements may interfere with the edges, thereby catching external objects. In addition, the edging 204 may vary in width 205 according to the predetermined pattern 206, the width measured from the peripheral contour 208 to the predetermined pattern 206, with some areas possibly more prone to catching or causing discomfort having a greater width than other areas less prone.

The main body 202 may define at least one opening 210 for inserting the brace component 110, 120 between the first and second faces 212, 214. The opening 210 may have an elastic periphery permitting the opening 210 to expand for insertion of the brace component 110, 120, and contract once the sleeve generally surrounds the brace components 110, 120. In addition, the main body 220 may define a slot 213 arranged to correspond with a strap of the brace component 110, 120 for the strap to pass therethrough.

Figure 4:
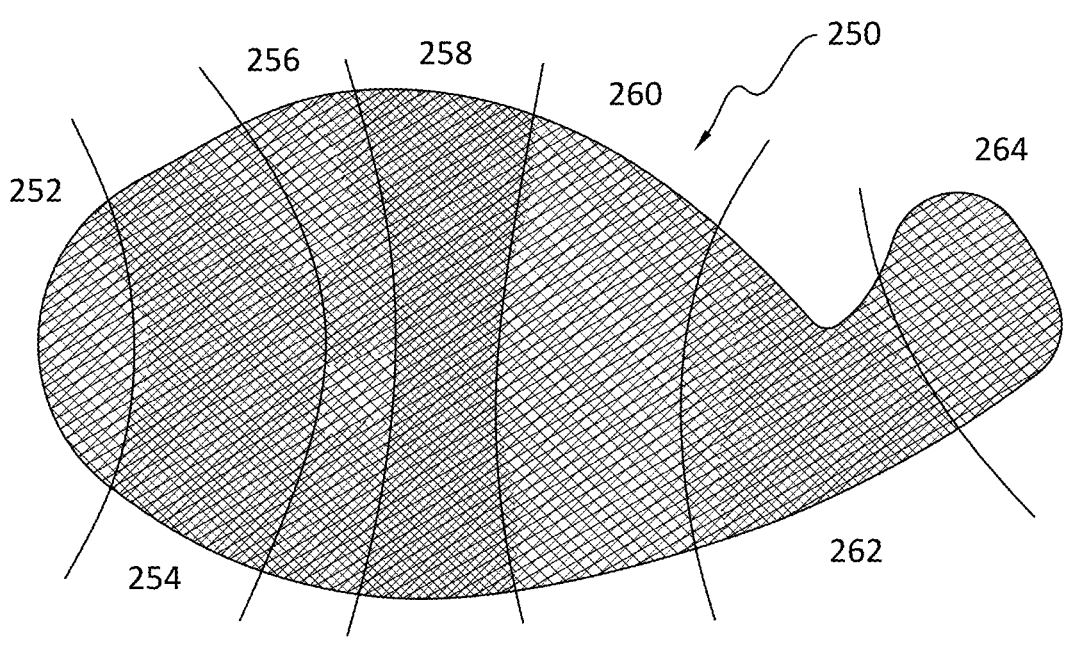
FIG. 4 is a schematic view of the brace component in FIG. 2, illustrating the dominance of flexure in using the orthopedic device in FIG. 1.

FIG. 4 illustrates a flexure gradient of the brace component 250 and how the predetermined pattern can be tailored according to the flexure gradient. The flexure gradient 258 is generally located at the center of the brace component, whereas areas 252, 254, 256, 260, 262 progressively reduce flexibility (as shown by the different shading), and the extension area 264 has its flexibility. The flexure gradient is useful in that the size of the frictional elements can be reduced in higher areas of flexibility. In contrast, areas of less flexibility, which are more likely to maintain consistent contact, may have larger frictional elements.

Figure 5:
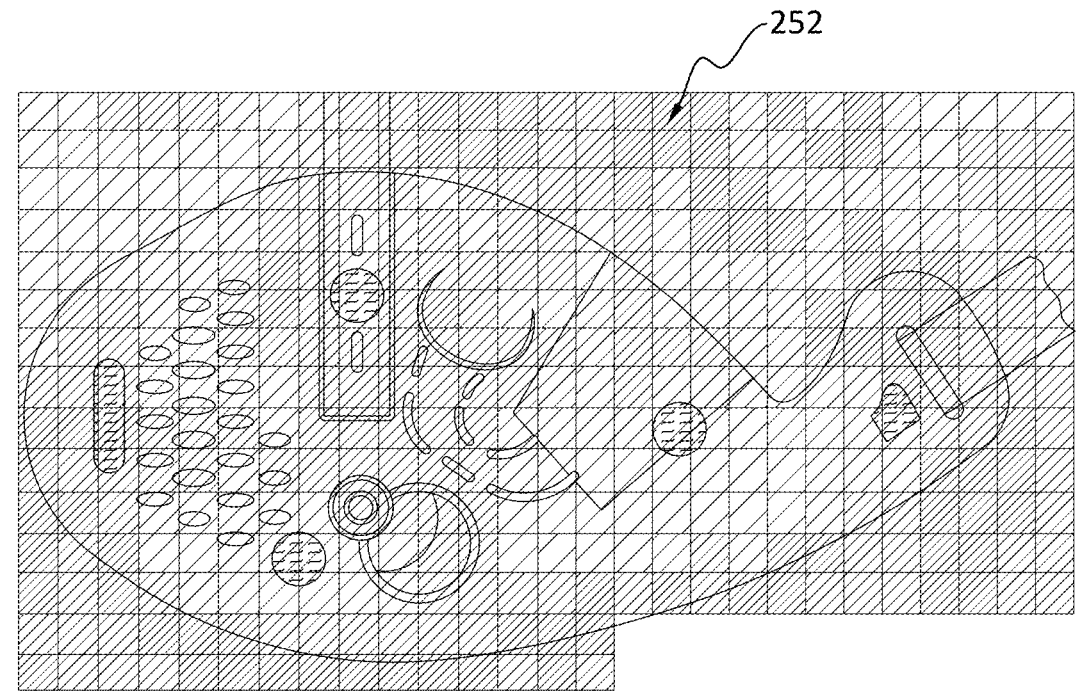
FIG. 5 is a schematic view of the brace component in FIG. 2 illustrating pressure mapping in the use of the orthopedic device in FIG. 1.

FIG. 5 exemplifies how pressure mapping can likewise be an aid in determining the predetermined pattern. The brace component 270 may have different pressure mapping with increased pressure at unique features of the brace component and exert less pressure elsewhere. The frictional elements may be sized according to where more pressure is exerted to create a more comfortable interface.

Figures 6A, 6B, 6C:
FIGS. 6A-6C are schematic views that exemplify different predetermined frictional elements produced according to the pressure mapping shown in FIG. 5.

FIGS. 6A-6C exemplify sleeves 280, 290, 300, and how they can be configured according to the flexure gradients and the pressure mapping, and accordingly tailor the predetermined patterns with regions of frictional elements generally having the same size.

FIG. 6A shows how different regions 282, 284, 286 may correspond to the representations in FIGS. 4 and 5, and such regions correspond to differently sized frictional elements at strategic locations in a more horizontal manner. FIG. 6B shows regions 292, 294, 296 more vertically according to the flexure gradients and pressure mapping. Finally, FIG. 6C shows how islands or larger regions 304, 306 can be surrounded by a region 302.

FIG. 9 illustrates a sleeve 330 with the different regions, as generally identified in FIGS. 6A-6C, have differently sized frictional elements 310, 312, 314, as illustrated in FIGS. 7A-7C, according to the grid of FIG. 8. Thus, the disclosure is not limited to these configurations and shapes of frictional elements despite the regions exemplified, shapes, and grid.

Figure 10:
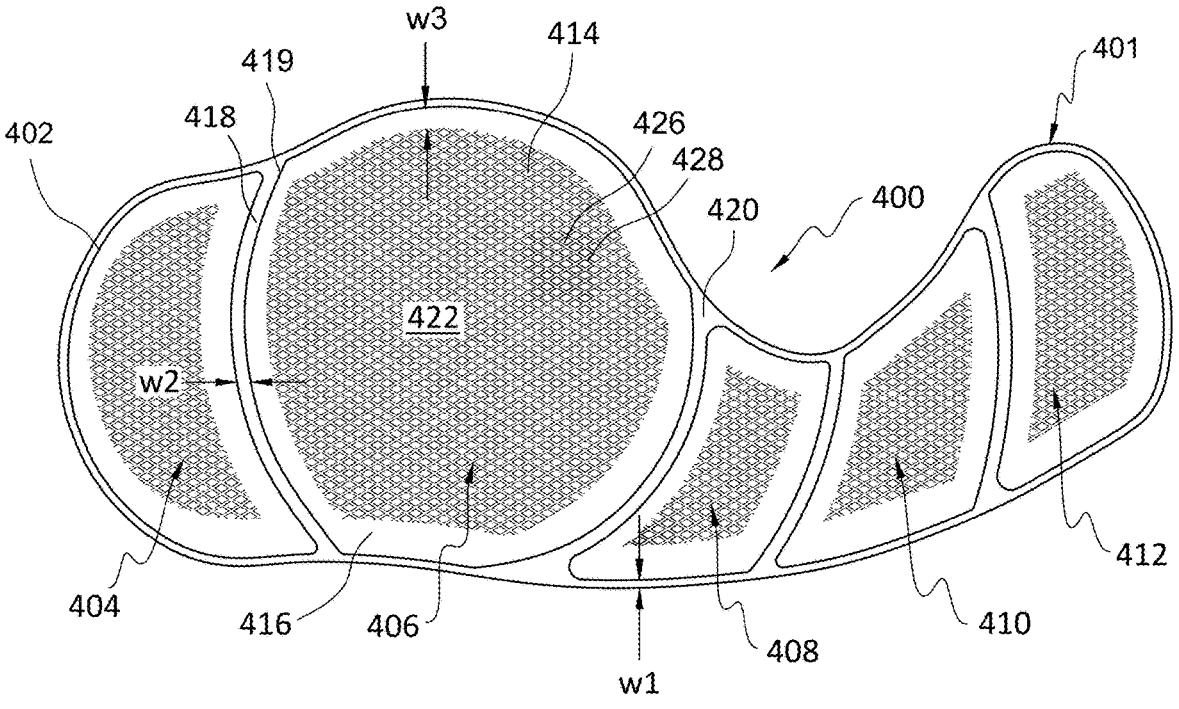
FIG. 10 is a plan view showing another embodiment of a liner pad.
Figure 11:
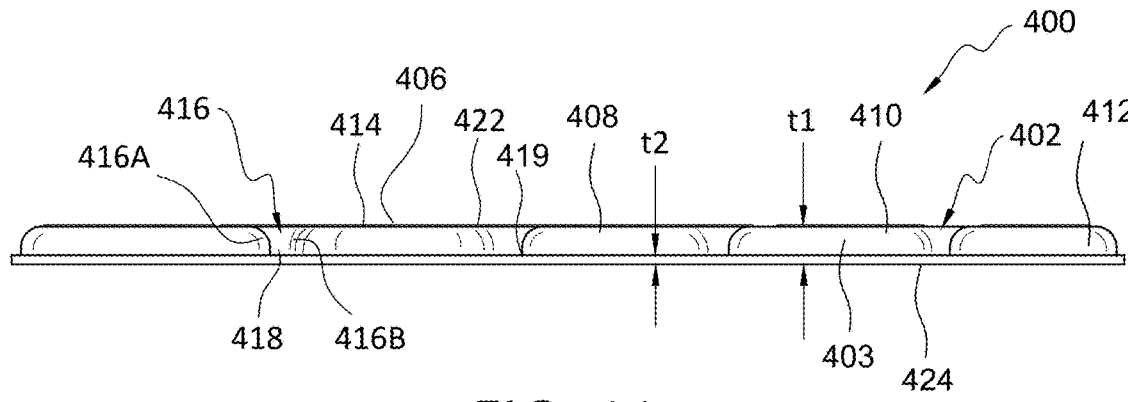
FIG. 11 is an elevational view of the liner pad of FIG. 10.

FIGS. 10 and 11 exemplify another sleeve or liner 400. The liner 400 has a peripheral edge 402 configured and dimensioned to correspond to a shape of a shell along which the liner 400 extends on an inner surface (not shown). The peripheral edge portion 402 comprises a substantially compressed liner region relative to pad regions 404, 406, 408, 410, 412. For example, the liner 400 has a core material 403 formed from foam, which may be open or closed cell, and preferably breathable in that air and moisture can extend from and between an inner surface 422 and an outer surface 424 of the liner 400.

Relative to the pad regions 404, 406, 408, 410, 412, generally having the same thickness t1, the peripheral edge portion 402 has a thickness t2 that is substantially less than the thickness t1. More specifically, the substantially smaller thickness of t2 versus t1 may be on order of at least half of the thickness of t1, and more preferably, t1 has a thickness at least three times the thickness of t2.

The peripheral edge portion 402 may have a width w1 of at least or at 1 mm from between pad regions 404, 406, 408, 410, 412, and an edge 402 of the periphery of the liner 400. The peripheral edge portion 402 may have a uniform width w1, or the width may vary depending on its location and proximity to different pad regions 404, 406, 408, 410, 412. The thickness t2 may likewise be uniform about the entirety of the periphery of the liner, or the thickness t2 may be variable. In each event, however, the peripheral edge portion 402 is constructed from the same core material 403 as the pad regions.

The different pad regions 404, 406, 408, 410, 412 preferably have a same height or thickness t1, although variations may have different heights or thicknesses. The pad regions 404, 406, 408, 410, 412 are separated by corresponding channels 418 that extend between pad regions 404, 406, 408, 410, 412. The channels facilitate contouring and may be determined in location and shape according to the discussion above regarding pressure mapping. The channels can therefore be provided to optimize contouring about the anatomy of the user and improve airflow for comfort.

The channels may have a width w2 that may vary depending on where they are located relative to the peripheral edge portion 402, in that at an opening 420 of the channels 418, the width w2 may be variable. In contrast, in a central portion, as shown by example in FIG. 10, the width w2 may have a segment with a substantially uniform width.

To effectuate a transition against the user, the pad regions may have variable, rounded, or otherwise shaped edges, as evidenced by transition edges 416, such as transition edges 416A, 416B spacing the contours of the channels 418. As shown in FIG. 10, each of the pad regions 404, 406, 408, 410, 412 may be shaped differently depending on where they may line up against the intended anatomy of a user.

The liner 400 has an inner surface 422 intended to be placed adjacent to a user and thereby serve as the interface between the inner surface of the shell and the user's anatomy. The liner 400 has an outer surface 424 that is intended to be placed adjacent to and secured against the inner surface of the shell. While not shown, the outer surface 424 may include hook and loop material that corresponds to hook and loop material on the inner surface of the shell to secure the liner 400 to the shell. For example, the outer surface 424 may be defined as an unbroken loop material disposed along an entirety or only segments of the core 403 and engageable with hook material along the shell.

The inner surface 422 includes or is defined by a frictional material, such as silicone, deposited along an outer surface of the pad regions 404, 406, 408, 410, 412, hereby defined as the frictional surface or layer, or a plurality of layers with each layer corresponding to one of the pad regions 414. The frictional material may likewise be considered frictional elements, as previously discussed. In a preferred embodiment, although not restricted thereto, the frictional surface 414 may have a lower profile defined at least in part by a minimal thickness, preferably less than 5 mm, more preferably less than 3 mm, and even more preferably less than 2 mm.

The lower profile of the frictional material has the advantage of being less aggressive on the user's skin, contrary to prior art liners or spacer elements. Likewise, because of the lower profile of the frictional material, it can be printed or otherwise formed along the surface of the core. Further, since the core is breathable over its entirety, there is no need to make the frictional surface 414 correspond exactly to apertures, as in prior art liners and spacer elements, since the pores or openings of the core material are many and diversely distributed, and further much smaller than apertures or openings formed by the frictional material. Thus, the liner can be manufactured at a lower cost due to the lack of need to make the frictional material exactly correspond to the inherent properties of the core.

The frictional surface 414 may form a predetermined pattern, such as the diamond shape pattern in FIG. 10, although the pattern is not limited to this configuration and may comprise different shapes either being uniform or variable depending on the location of the pad region and the corresponding anatomy on the user. Different pad regions may have the same pattern of the frictional material, or may omit the frictional material, such as pad region 406 having frictional material, whereas pad region 412 may omit the frictional material.

The predetermined pattern forms apertures or openings 426 that extend substantially more over the surface area of the pad regions over the portion of the frictional material that may form solid structures 428, such as the depicted lines. The apertures or openings 426 extend at least twice the surface area of the core versus the portion of the frictional material as solid structures 428 over the core, thus enabling the frictional material to be printed, laminated, or otherwise disposed over the core without concern for impeding breathability of the core. The relative surface area of the apertures or openings 426 over the core versus the frictional material solid structures 428 has the further advantage of minimizing care of the liner since it is easier for dust, dirt, and debris to be removed or slip away from the liner in use, as the minimization of frictional material limits the tackiness of the liner, which provides a sufficient amount to prevent migration over the anatomy of the user.

As shown in FIGS. 10 and 11, the frictional surface 414 may not extend over the transition edges 416 of the pad regions, similar to the aforementioned edging 204, such that the relationship of the frictional surface 414 may be similar to any of the aforementioned embodiments. For example, the frictional surface 214 may terminate a width w3 from the peripheral edge 419 of the pad region 404, or the width w3 may comprise the width of the transition edge, particularly when viewed from a plan view, as in FIG. 10.

For example, the frictional surface 414, as shown in FIG. 11, may form a planar surface over corresponding planar surfaces identified by 422 of the pad regions 404, 406, 408, 410, 412. The omission of the frictional surface 414 over the transition edges 416 reduces the risk of skin irritation and forms a cleaner finish to the final liner. Further, the planar surface formed or represented by 422 may be thermoformed so there is even pressure applied by the liner against the user.

While the frictional surface 414 may be preferably silicone, it can be formed according to any of the means discussed above in connection with preceding embodiments. Moreover, at least with the embodiment of FIGS. 10 and 11, the frictional surface 414 is preferably continuous in that it forms a film that is a continuous structure, in contradistinction to the possibility of preceding embodiments whereby the frictional material is formed by discrete elements. For example, as the frictional surface is preferably continuous, it could be removed or placed over the core as a single layer or substrate. Indeed, the frictional surface may be a layer that is at least partially cured and then placed over the surface of the core in a single step, with the frictional material curing and interlocking with the material of the core. Each pad region can have a different layer or frictional surface, with a different or the same predetermined pattern as the other pad region.

The embodiments and methods for determining the patterns and shapes of the frictional elements provide improved comfort characteristics due to their consideration given at least flexure gradients and pressure mapping of a corresponding brace component. The concepts of the sleeve can be extended to other articles employing the same criteria or including different or additional criteria to improve migration control and comfort.

It is understood that not all objects or advantages may be achieved under any embodiment of the disclosure. Those skilled in the art will recognize that the sleeve may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct a sleeve by principles of the present disclosure. The skilled artisan will understand that the features described herein may be adapted to other types of articles. Hence this disclosure and the embodiments and variations thereof are not limited to orthopedic devices.

The invention claimed is:

1. An orthopedic device comprising a brace component and a sleeve or liner for the brace component, wherein the brace component is formed as a shell having rigid or semi-rigid properties, the shell defining a peripheral contour and a flexure gradient including a plurality of shell regions having different flexural stiffnesses;

wherein the sleeve or liner has a main body defining a peripheral contour arranged at least approximately to the peripheral contour of the shell and sized to correspond thereto, the main body of the sleeve or liner defining first and second opposing faces that are secured together along at least a portion of a peripheral edge of the main body of the sleeve or liner; and

frictional material disposed on one of the first and second opposing faces of the main body of the sleeve or liner to define a predetermined pattern of frictional elements including at least a first set of frictional elements and a second set of frictional elements, the frictional elements of the first and second sets having different, respective sizes or shapes and being positioned on the main body of the sleeve or liner at locations corresponding to different shell regions of the flexure gradient;

wherein the frictional elements of the first set are disposed at locations corresponding to shell regions of lower flexural stiffness, and wherein the frictional elements of the second set are disposed at locations corresponding to shell regions of higher flexural stiffness, and wherein the predetermined pattern of frictional elements varies in size or shape in correspondence with the flexure gradient of the shell.

2. The orthopedic device of claim 1, wherein the main body of the sleeve or liner corresponds in shape to an extension extending from a main body of the shell by a junction such that the sleeve or liner covers an entirety of the shell about the peripheral contour thereof.

3. The orthopedic device of claim 1, wherein frictional elements of the first and second sets protrude from the main body by a same thickness.

4. The orthopedic device of claim 1, wherein frictional elements of the first and second sets protrude from the main body by different, respective thicknesses.

5. The orthopedic device of claim 1, wherein frictional elements of the first and second sets define a same shape.

6. The orthopedic device of claim 1, wherein frictional elements of the first and second sets define an oval shape and differ from one another at least in size.

7. The orthopedic device of claim 6, wherein the oval shape is elongated along a length of the sleeve or liner.

8. The orthopedic device of claim 1, wherein the predetermined pattern of frictional elements defines at least first and second rows of frictional elements, the first row being staggered in a height direction of the sleeve or liner relative to the second row with a spacing such that frictional elements of the first row align between frictional elements of the second row.

9. The orthopedic device of claim 1, further comprising an edging surrounding the predetermined pattern of frictional elements and devoid of the frictional material.

10. The orthopedic device of claim 9, wherein the edging varies in width as measured from the peripheral contour of the main body to the predetermined pattern about the peripheral contour.

11. The orthopedic device of claim 1, wherein the other of the first and second opposing faces opposite the one carrying the frictional material is configured without frictional elements.

12. The orthopedic device of claim 1, wherein the sleeve or liner is formed from a textile material.

13. The orthopedic device of claim 12, wherein the textile material is arranged to permit air and moisture transfer through the main body between the first and second opposing faces.

14. The orthopedic device of claim 12, wherein the sleeve or liner is formed from a textile material that is breathable and elastic.

15. The orthopedic device of claim 1, wherein the sleeve or liner comprises a laminated structure including a core material and an outer surface layer, the outer surface layer comprising unbroken loop material configured to engage a complementary fastening material on an inner surface of the shell.

* * * * *